United States Patent [19]

Fischer et al.

[11] 4,313,838

[45] Feb. 2, 1982

[54] PREPARATION AND USE OF XANTHOGEN CHLOROPROPYL FORMATE FLOTATION REAGENTS

[76] Inventors: Arthur H. Fischer, 1115 Fifth Ave., New York, N.Y. 10028; Lawrence E. Strow, 6507 Lawyers Hill Rd., Baltimore, Md. 21227; Franklin A. Bolth, 516 Dunkirk Rd., Baltimore, Md. 21212

[21] Appl. No.: 31,317

[22] Filed: Apr. 19, 1979

Related U.S. Application Data

[62] Division of Ser. No. 872,562, Jan. 26, 1978.

[51] Int. Cl.$^3$ .................. C07C 154/02; C07C 69/003
[52] U.S. Cl. .................................. 252/60; 260/455 B; 260/453 R; 260/463
[58] Field of Search ............... 260/455 B, 453 R, 463; 252/60

[56] References Cited

U.S. PATENT DOCUMENTS 1,684,536  9/1928  Fischer ............................ 260/455 B
2,608,573  8/1952  Fischer ............................ 260/455 B
2,678,939  5/1954  McCool ........................... 260/455 B

OTHER PUBLICATIONS

Handbook of Chemistry and Physics, 46th Edition, 1965–1966.

*Primary Examiner*—John M. Ford
*Assistant Examiner*—Robert C. Whittenbaugh

[57] ABSTRACT

Flotation of copper sulfide ores in acid circuits has historically been promoted with ethyl xanthogen ethyl formate. Significantly improved results are achieved with the reaction product of ethyl or isopropyl zanthate with a chlorinated chloroformate. Sodium ethyl or isopropyl zanthate is prepared in an all-liquid system in the presence of excess alcohol. Chlorinated isopropyl chloroformate is prepared by reaction of phosgene and propylene epoxide in the presence of performed product as deluent and activated carbon as catalyst. The chloroformate and xanthate-alcohol mixture are reacted, and the alcohol may be recovered from the aqueous phase.

5 Claims, No Drawings

PREPARATION AND USE OF XANTHOGEN CHLOROPROPYL FORMATE FLOTATION REAGENTS

This is a division, of application Ser. No. 872,562, filed Jan. 26, 1978.

BACKGROUND OF THE INVENTION

The present invention relates generally to the preparation and use of xanthogen formate flotation promoters and, more particularly, to alkyl xanthogen 2-chloropropyl formates, wherein the alkyl group contains 2-6 carbon atoms.

Alkyl xanthogen ethyl formates have long been successfully employed as mineral collectors in a broad range of ore flotation operations. In acid circuit and leach-precipitation-float operations, they have proven unique and defied repeated attempts to replace them.

The present invention provides a new composition which offers a significantly improved metallurgical performance. The results of comparative tests on various samples of copper sulfide ore from a large mining operation employing ethyl xanthogen ethyl formate illustrate this performance.

While the ethyl xanthogen ethyl formate has been an industry mainstay, variations are known and have been successful in specific instances.

U.S. Pat. No. 1,684,536 of Fischer discloses the reaction of xanthates with certain acid chlorides, the product being a useful flotation reagent. Ethyl chlorocarbonate, acetyl chloride, carbonyl chloride and sulfuryl chloride are disclosed.

U.S. Pat. No. 2,412,500 of Fischer discloses unsymmetrical alkyl xanthogen formates, most particularly amyl and hexyl xanthogen ethyl formates, as flotation agents.

U.S. Pat. No. 2,608,573 of Fischer discloses reaction of a potassium ethyl xanthate with chloro ethyl chloroformate to produce ethyl xanthogen chloro ethyl formate, with a 95% yield.

OBJECTS OF THE INVENTION

A general object of the present invention is to provide an improved flotation reagent of the xanthogen formate type.

A further object of the present invention is to provide a new method of preparing alkyl xanthogen chloropropyl formates.

Another object of the present invention is to provide a method of flotation using alkyl xanthogen 2-chloropropyl formates or, more accurately, the insoluble reaction product of an alkali metal lower alkyl xanthate and 2-chloropropyl chloroformate.

Various other objects and advantages of the invention will become clear from the following description of embodiments, and the novel features will be particularly pointed out in connection with the appended claims.

DESCRIPTION OF EMBODIMENTS

In the flotation of copper sulfide ores, operators are constantly alert to reducing metal losses in tailings, increasing the copper content of the concentrate and thus improving overall recovery. Improvements of as little as a tenth of a percent are economically and technically significant.

In one aspect, the present invention is based on the significantly improved results, compared to ethyl xanthogen ethyl formate, in copper sulfide flotation. As detailed in the examples set forth below, the degree of improvement (in terms of percent recovery) ranges from about 1% to an extraordinary 8%. In another aspect, the novel flotation reagent, while generally characterized as a lower alkyl xanthogen 2-chloropropyl formate, is really—and is so claimed—the insoluble reaction product of an alkali metal lower alkyl xanthate and 2-chloropropyl chloroformate. This is so because it is known that there are other compounds in the reaction product, though they have not all been identified. Lastly, the xanthate and the chloroformate are prepared in a particular manner distinct from previously known methods, and the reaction of the two is also carried out in a novel manner. Thus, it is not known whether the extraordinary results achieved by the invention are attributable to the activity of lower alkyl xanthogen chloropropyl formate per se, the presence of unidentified other compounds, or the results of the specific process steps employed.

Preparation of the Xanthate

The classic reaction for formation of xanthates is as follows:

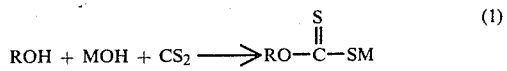

$$ROH + MOH + CS_2 \longrightarrow RO-\overset{\overset{\displaystyle S}{\|}}{C}-SM \qquad (1)$$

In this reaction R is a lower alkyl radical with 2-6 carbon atoms, and M is an alkali metal, sodium or potassium, almost universally sodium.

It is known, that if one introduces sufficient water into ethyl alcohol to dissolve all caustic, the yield of xanthate is a disappointing and uneconomical 70-72%. However, what was discovered and considered surprising, was that if alcohol is used in a very substantial excess with a minimum of added water, the reaction goes substantially to completion, but with all products still in the liquid phase. This is successful with as little as 20% excess alcohol, but as much as 600% has been used, depending on the alcohol. Primarily for economic reasons, with ethyl alcohol an excess of 150% is preferred (e.g. an additional 1.5 moles ROH for each mole required for the reaction).

When the xanthate-alcohol solution is used to produce a final end product (xanthogen formate), the latter reaction product is an insoluble oily phase that separates from the aqueous phase, and the excess alcohol is dissolved in the water, making recovery, if desired, simple. Recovery of the alcohol may be effected in a still of 10 theoretical plates. Strong brine is discarded at the bottom and 80% or higher ROH is condensed from the top for reuse. Moreover, the presence of the alcohol does not affect the reaction of xanthate with chloroformate and, of course, having all reactants in the liquid phase is a distinct advantage.

The following small-scale example is meant to be illustrative, and should not be interpreted in a limiting sense.

In a suitable glass mixing flask the following were mixed and cooled back to 25° C.
  240.0 gr of 50% Caustic Soda solution
  361.8 gr of 95.5% ethyl alcohol
  50.0 gr of water Following the return of the temperature of 25° C., 224 gr of carbon disulfide was added slowly at a temperature of 25°–26° C. in 10 minutes. After 1.5 hours the preparation was considered complete and the mix was further diluted with 200 ml. of water to prevent solidification of the product.

Preparation of Chloroformate

The reaction of phosgene with an epoxide is written as follows:

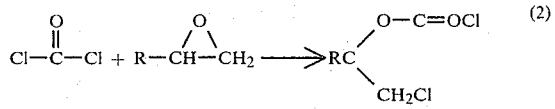

(2)

In this equation, R may be hydrogen, lower alkyl, or another organic group. Prior workers have used solvents, low temperatures and continually renewed catalysts, and still suffer low yields.

It has been determined that Reaction 2 is catalyzed to a remarkable degree by activated carbon, in either pellet or powder form. Even more surprising, the catalyst does not appear to lose activity with time (e.g. a 10-kilogram run). Further, Reaction 2 can be run substantially to completion (with the carbon catalyst) at temperatures an order of magnitude higher than contemplated by prior workers, provided the heat of reaction is effectively absorbed. The higher temperature, of course, has the expected increased rate of reaction. Necessary temperature control is effected by using a large quantity of the final product as a temperature-moderating medium, so that the concentration of reactants at any one time or point is kept low. This, plus relatively moderate cooling, serve to maintain the reaction temperature in the desired range of 60° to 125° C.

It is to be noted that prior workers with epoxides used low temperatures both to minimize byproducts and to keep the reaction under control by preventing boiling-off of solvents and catalysts. Further, in the better-known reactions with alcohols, a certain amount of HCl is necessarily produced, and its vaporization removes some of the reaction energy. Thus, in the present invention, the absence of HCl either as a byproduct or catalyst would seem to worsen control problems, but the use of the permanent carbon catalyst, high reaction temperatures and circulating chloroformate coolant combine to produce an improved and, more importantly continuous process.

A large flask was used as a reservoir underneath a glass column packed with 4–8 mesh activated carbon granules. A controlled volume pump pumped a flow of preformed chloroformate up through a heat exchanger to the top of the glass catalyst tower. There, it dissolved and mixed with an incoming feed of propylene epoxide and phosgene and fell immediately upon the catalyst. Product could either be accumulated in the bottom flask or removed continuously from the pump line.

The feed and re-circulation ratios were varied to find the optimum mixtures as well as the overall reaction rate. Temperatures were measured in the catalyst bed at top and bottom. It was found that temperatures above 115° C. were marginally harmful to yield and quality, and that temperatures over 125° C. were definitely harmful, producing hydrogen chloride gas, water and other undesired products. A catalyst charge of 88 grams of carbon was used without a change in activity to make over 10 kilos of 2-chloroisopropyl chloroformate.

Table I illustrates results in a continuous flow preparation of 2-chloroisopropyl chloroformate through a 22" long by 1" diameter insulated catalyst column packed with 4–8 mesh catalytic grade carbon granules. The feed was an equimolar ratio of phosgene and propylene epoxide, and all products had a purity of about 97%. As previously noted, the product chloroformate was re-circulated by a pump at a ratio varied as noted. There was no external heat transfer in the catalyst column.

TABLE I

| | Continuous Tests | | | |
|---|---|---|---|---|
| Test | Ratio, Recirculation to Raw Material | Producton Rate Gr./Hr. | Highest C. Temp. | Weight % Yield |
| 1 | 10.3 | 274 | 93 | 98.9 |
| 2 | 6.4 | 284 | 106 | 99.6 |
| 3 | 5.5 | 573 | 120 | 88.9 |
| 4 | 5.1 | 404 | 125 | 90.7 |
| 5 | 4.8 | 400 | 127 | 90.8 |
| 6 | 6.9 | 248 | 113 | 90.8 |
| 7 | 12.1 | 300 | 85 | 97.7 |

Reaction of Xanthate and Chloroformate

The preparation of the flotation reagent in accordance with the invention differs from known practices primarily in the fact that it is carried out in the presence of the excess alcohol used during the xanthate formation.

A solution of the sodium alkyl xanthate was reacted with 2-chloroisopropyl chloroformate between the temperatures of 25° and 45° C. The reaction product and its aqueous salt solution were stirred at 45° C. for one hour to complete the reaction. The mixing of the reagents may be done by adding the chloroformate to the xanthate solution, but it is preferable to add the xanthate solution to the chloroformate to reduce the formation of by-products. Sufficient water must be used to dissolve the sodium chloride formed.

The reaction product, a water-insoluble yellow oil, is washed with fresh water a and separated in order to remove small amounts of salt and soluble by-products.

The xanthates used may be made from various alcohols such as ethyl, isopropyl, n-propyl, n-butyl, isobutyl, sec.-butyl, amyl, or hexyl alcohol. There is very little difference in procedure or product appearance with any of the above alkyl xanthates. Ethyl and isopropyl types are illustrated in the following examples.

EXAMPLE I

An industrial-grade solution having an assay of 540 grams per liter of sodium ethyl xanthate in a mixture of ethyl alcohol and water was obtained by the procedures set forth hereinabove. This solution also contains some impurities in the form of sodium carbonate, sodium trithiocarbonate, and free sodium hydroxide. A 320 ml. volume of this solution along with 200 ml. of water were reacted in standard laboratory equipment with 159.5 grams of 2-chloro isopropyl chloroformate. After Washing, 230 grams of oil were recovered. Gas chromatographic analysis showed a minimum of 10 compounds present, including carbon disulfide, diethyl xanthic anhydride, ethyl 2-chloro isopropyl carbonate, and ethyl xanthogen 2-chloro isopropyl formate. Several others were not identified.

EXAMPLE II

An industrial grade solution having an assay of 365 grams per liter of sodium isopropyl xanthate in water was obtained. This solution also contains the same impurities described in Example I. About 433.5 ml. of this solution was treated with 5.8 grams of 95% sulfuric acid and thereafter reacted with 159.7 grams of 2-chloro isopropyl chloroformate. After washing, 251.5 grams of oil were recovered. Gas chromatographic analysis showed a minimum of 6 compounds present some of which were analogs of those described in Example I.

Flotation Tests

Extensive testing was carried out to compare reagents of the present invention—the reaction product of sodium ethyl or isopropyl xanthate and 2-chloro isopropyl chloroformate—with ethyl xanthogen ethyl formate.

In the following examples, Table II, sulfide ores of the composition indicated with respect to copper, were ground in water to form aqueous pulps and subjected to froth flotation operations in the presence of the reagents indicated but, otherwise, under identical conditions standard for this operation, with the production of concentrate and tailing products of the analyses indicated. Minerec A is a commercial reagent which is the reaction product of sodium ethyl xanthate and ethyl chloroformate. Composition B is the reaction product of sodium ethyl xanthate and 2-chloro isopropyl chloroformate, which could be characterized as ethyl xanthogen 2-chloro isopropyl formate plus impurities.

TABLE II

| Example No. | Ore % Cu | Minerec A Concentrate % Cu | Minerec A Tailing % Cu | Minerec A Recovery % | Composition B Concentrate % Cu | Composition B Tailing % Cu | Recovery % |
|---|---|---|---|---|---|---|---|
| 1 | 1.37 | 13.18 | .403 | 72.85 | 13.00 | .355 | 76.20 |
| 2 | 1.61 | 13.16 | .342 | 80.87 | 12.59 | .320 | 82.24 |
| 3 | 1.37 | 12.27 | .347 | 76.86 | 11.07 | .283 | 81.75 |
| 4 | 1.58 | 12.77 | .302 | 82.85 | 12.59 | .267 | 84.75 |
| 5 | 1.52 | 14.17 | .260 | 84.47 | 14.43 | .248 | 85.13 |
| 6 | 1.59 | 15.94 | .211 | 88.05 | 16.04 | .196 | 88.68 |
| 7 | 1.68 | 13.43 | .206 | 89.05 | 14.88 | .193 | 89.64 |

Ore samples in Examples 1–4 were from one section of the mine where ore is particularly refractory, and improvement with Composition B is exceptional. Samples 5–7 were from another, somewhat less refractory section and the degree of improvement, while less, is still significant.

In the tests listed in Table III, composition C is the reaction product of sodium isopropyl xanthate and 2-chloro isopropyl chloroformate, which can be characterized as isopropyl xanthogen 2-chloro isopropyl formate plus impurities.

TABLE III

| Example # | Ore % Cu | Minerec A Conc. % Cu | Minerec A Tail % Cu | Minerec A Recovery % Cu | Composition C Conc. % Cu | Composition C Tail % Cu | Composition C Recovery % Cu |
|---|---|---|---|---|---|---|---|
| 8 | 1.80 | 18.94 | .265 | 86.50 | 17.41 | .256 | 87.06 |
| 9 | 1.86 | 17.69 | .254 | 87.58 | 17.90 | .246 | 87.96 |
| 10 | 1.65 | 15.03 | .211 | 88.42 | 14.72 | .201 | 89.03 |
| 11 | 1.59 | 15.14 | .255 | 87.17 | 15.60 | .206 | 88.18 |
| 12 | 1.61 | 16.65 | .256 | 85.40 | 15.18 | .242 | 86.34 |

Those skilled in the art will appreciate that, in Examples 1–12, other reagents were also employed; what is important is that all conditions were held constant except for the formate compositions. However, in order to establish that it is indeed the composition of the invention and nothing else that is responsible for the improved results, Examples 13–15 below indicate all reagents used, and their amounts, on three separate ores. Composition B is the same as used in Examples 1–12.

Examples with Other Ores

EXAMPLE 13

Ore assaying 1.045% Cu

| | | |
|---|---|---|
| Concentrate, % Cu | 7.94 | 7.41 |
| Tailing % Cu | .226 | .134 |
| % Recovery | 80.29 | 88.78 |
| Reagents: Lbs per ton | | |
| Sulphuric Acid | 8.0 | 8.0 |
| Pine oil | .06 | .06 |
| Minerec A | .10 | — |
| Composition B | — | .10 |

EXAMPLE 14

Ore assaying 0.890% Cu

| | | |
|---|---|---|
| Concentrate, % Cu | 10.17 | 10.37 |
| Tailing % Cu | .235 | .205 |
| % Recovery | 75.40 | 78.65 |
| Reagents: Lbs per ton | | |
| Lime | 5.0 | 5.0 |
| Cresylic Acid | .40 | .40 |
| Minerec A | .02 | — |
| Composition B | — | .02 |

It is to be noted that Example 14 establishes utility of the invention in basic flotation circuits.

EXAMPLE 15

Ore assying 1.443% Cu subjected to L.P.F. treatment

| | | |
|---|---|---|
| Concentrate, % Cu | 6.43 | 6.63 |
| Tailing % Cu | .365 | .220 |
| % Recovery | 79.22 | 87.85 |
| Reagents: Lbs. per ton | | |
| Sulphuric Acid | 16.0 | 16.0 |
| Pine oil | .10 | .10 |
| Minerec A | .25 | — |

| | |
|---|---|
| -continued | |
| Composition B | — .25 |

Example 15 shows truly remarkable results for an ore subjected to the leach-precipitation-flotation process, though it would be presumptive to conclude that similar results would be obtained in all cases. As can be seen, even under closely controlled laboratory conditions, the degree of improvement varies. This is to be expected in any ore body. What is significant, of course, is that there was a substantial improvement in each case.

Various changes in the details, steps, materials and arrangements of parts, which have been herein described and illustrated to explain the nature of the invention, may be made by those skilled in the art within the principle and scope of the invention as defined in the appended claims.

What is claimed is:

1. A process for preparing a xanthogen-formate bearing flotation agent, which comprises:
reacting 2-chloro isopropyl chloroformate with an alkali-metal alkyl xanthate having 2 to 6 carbons in the alkyl group in a solvent mixture of water and alcohol which is sufficient to dissolve said chloroformate and xanthate,
wherein said alcohol has the same number of carbons as said alkyl group, and
wherein said chloroformate is the reaction product of phosgene and isopropyl epoxide carried out in the presence of activated carbon as catalyst and preformed chloroformate as diluent and heat absorber.

2. The process as claimed in claim 1, wherein the ratio of preformed chloroformate to reactants is at least 4:1, and the phosgene, isopropyl epoxide reaction temperature is maintained in the range of 60° to 125° C.

3. The process for preparation of a flotation reagent containing a lower alkyl xanthogen isopropyl formate comprising:
reacting a lower alkyl alcohol having 2–6 carbon atoms in the alkyl group with an alkali metal hydroxide and carbon disulfide in solution and in the presence of a molar excess of said alcohol to produce an excess-alcohol containing solution of an alkali metal lower alkyl xanthate;
reacting phosgene and isopropyl epoxide in the presence of activated carbon and a diluent and heat absorber to produce 2-chloro isopropyl chloroformate, said diluent and heat absorber being preformed chloroformate;
reacting said chloroformate with said xanthate solution to produce a water-insoluble oily phase containing said xanthogen formate and an aqueous phase containing said alcohol; and
recovering said oily phase.

4. The process as claimed in claim 3, wherein the excess of said alcohol is in the range of 20 to 600%.

5. The process as claimed in claim 3, wherein the ratio of preformed chloroformate to said phosgene and epoxide reactants is at least 4:1.

* * * * *